United States Patent [19]

Cai et al.

[11] Patent Number: 6,153,591
[45] Date of Patent: Nov. 28, 2000

[54] DIPEPTIDE CASPASE INHIBITORS AND THE USE THEREOF

[75] Inventors: Sui Xiong Cai, San Diego; John Drewe, Costa Mesa; Yan Wang; Eckard Weber, both of San Diego, all of Calif.

[73] Assignee: Cytovia, Inc., San Diego, Calif.

[21] Appl. No.: 09/270,735

[22] Filed: Mar. 16, 1999

Related U.S. Application Data

[60] Provisional application No. 60/078,051, Aug. 16, 1998, abandoned.

[51] Int. Cl.[7] .............................. A01N 1/02; A01N 3/00; A61K 38/05; C07K 5/06
[52] U.S. Cl. ............................ 514/19; 435/1.1; 435/1.2; 435/2; 548/200; 549/76; 549/77; 549/493; 549/494; 560/37; 560/38; 560/39; 560/40; 560/41; 560/42; 560/125; 560/169; 562/442; 562/443; 562/444; 562/445; 562/448; 562/449
[58] Field of Search ............................. 514/19; 435/1.1, 435/1.2, 1.3, 2; 549/76, 77, 493, 494, 37, 38, 39, 40, 41, 42, 125, 169; 562/442, 443, 444, 445, 448, 449, 451, 507, 561, 564; 548/200

[56] References Cited

U.S. PATENT DOCUMENTS

| | | | |
|---|---|---|---|
| 4,153,688 | 5/1979 | Domicoli et al. | 424/177 |
| 4,518,528 | 5/1985 | Rasnick | 260/112.5 |
| 5,416,013 | 5/1995 | Black et al. | 435/226 |
| 5,430,128 | 7/1995 | Chapman et al. | 530/330 |
| 5,434,248 | 7/1995 | Chapman et al. | 530/330 |
| 5,462,939 | 10/1995 | Dolle et al. | 514/231.5 |
| 5,585,357 | 12/1996 | Dolle et al. | 514/18 |
| 5,677,283 | 10/1997 | Dolle et al. | 514/18 |
| 5,756,465 | 5/1998 | Sleath et al. | 514/17 |
| 5,843,904 | 12/1998 | Bemis et al. | 514/18 |
| 5,866,545 | 2/1999 | Hagmann et al. | 514/18 |
| 5,869,519 | 2/1999 | Karanewsky et al. | 514/415 |
| 5,932,549 | 8/1999 | Allen et al. | 514/18 |

FOREIGN PATENT DOCUMENTS

| | | |
|---|---|---|
| 0 519 748 A2 | 12/1992 | European Pat. Off. . |
| 0 618 223 A2 | 10/1994 | European Pat. Off. . |
| WO 93/05071 | 3/1993 | WIPO . |
| WO 96/03982 | 2/1996 | WIPO . |
| WO 96/20721 | 7/1996 | WIPO . |
| WO 98/10778 | 3/1998 | WIPO . |
| WO 98/11109 | 3/1998 | WIPO . |
| 98/41232 | 9/1998 | WIPO . |
| WO 99/18781 | 4/1999 | WIPO . |

OTHER PUBLICATIONS

Alnemri, E.S. et al., "Human ICE/CED–3 Protease Nomenclature," *Cell* 87:171 (1996).

Angliker, H. et al., "The synthesis of lyslylfluoromethanes and their properties as inhibitors of trypsin, plasmin and cathepsin B," *Biochem J.* 241:871–875 (1987).

Black, R.A. et al., A Pre–aspartate–specific Protease from Human Leukocytes That Cleaves Pro–interleukin–1β, *J. Biol. Chem.* 264:5323–5326 (1989).

Black, S.C. et al., "Co–Localization of the Cysteine Protease Caspase–3 with Apoptotic Myocytes after In Vivo Myocardial Ischemia and Reperfusion in the Rat," *J. Mol. Cell. Cardiol.* 30:733–742 (Apr. 1998).

Bourne, E.J. et al., "Studies of Trifluoroacetic Acid. Part XVIII. Reaction of N–Aroylglycines with Perfluoro–carboxylic Anhydrides." *J. Chem. Soc. Part II*:1771–1775 (1961).

Conaldi, P.G. et al., "HIV–1 Kills Renal Tubular Epithelial Cells In Vitro by Triggering an Apoptotic Pathway Involving Caspase Activation and Fas Upregulation," *J. Clin. Invest.* 102:2041–2049 (Dec. 1998).

del Pozo, O., and Lam, E., "Caspases and programmed cell death in the hypersensitive response of plants to pathogens," *Curr. Biol.* 8:1129–1132 (Sep. 1998).

di Giovine, F.S., and Duff, G.W., "Interleukin 1: the first interleukin," *Immunology Today* 11:13–14 (1990).

Dinarello, C. A., "Interleukin–1 and Interleukin–1 Antagonism," *Blood* 77:1627–1652 (1991).

Dolle, R.E. et al., "P$_1$ Aspartate–Based Peptide α–((2, 6–Dichlorobenzoyl)oxy)methyl Ketones as Potent Time–Dependent Inhibitors of Interleukin–1β–Converting Enzyme," *J. Med. Chem.* 37:563–564 (1994).

Emery, E. et al., "Apoptosis after traumatic human spinal cord injury," *J. Neurosurg.* 89:911–920 (Dec. 1998).

Goldberg, Y.P. et al., "Cleavage of huntingtin by apopain, a proapoptotic cysteine protease, is modulated by the polyglutamine tract," *Nature Genetics* 13:442–449 (1996).

Greenberg, J.T. et al., "Programmed Cell Death in Plants: A Pathogen–Triggered Response Activated Coordiantely with Multiple Defense Functions," *Cell* 77:551–563 (1994).

Hiraoka, J. et al., "Participation of apoptosis in renal amyloidosis," *Jpn. J. Nephrol.* 40:276–283 (May 1998).

(List continued on next page.)

*Primary Examiner*—Jeffrey E. Russel
*Attorney, Agent, or Firm*—Sterne, Kessler, Goldstein & Fox P.L.L.C.

[57] ABSTRACT

The present invention is directed to novel dipeptides represented by the general Formula I:

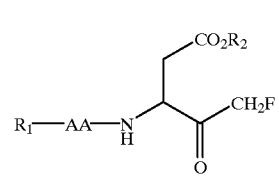

where $R_1$–$R_2$ and AA are defined herein. The present invention relates to the discovery that compounds having Formula I are potent inhibitors of caspases and apoptotic cell death. Therefore, the inhibitors of this invention can retard or block cell death in a variety of clinical conditions in which the loss of cells, tissues or entire organs occurs.

49 Claims, No Drawings

OTHER PUBLICATIONS

Jaeschke, H. et al., "Activation of Caspase 3 (CPP32)–Like Proteases Is Essential for TNF–α–Induced Hepatic Parenchymal Cell Apoptosis and Neutrophil–Mediated Necrosis in a Murine Endotoxin Shock Model," *J. Immun.* 160:3480–3486 (Apr. 1998).

Jones, R.A. et al., "Fas–Mediated Apoptosis in Mouse Hepatocytes Involves the Processing and Activation of Caspases," *Hepatology* 27:1632–1642 (Jun. 1998).

Kermer, P. et al., "Inhibition of CPP32–Like Proteases Rescues Axotomized Retinal Ganglion Cells from Secondary Cell Death In Vivo," *J. Neuroscience* 18:4656–4662 (Jun. 1998).

Kubo, S. et al., "Hepatocyte injury in tyrosinemia type 1 is induced by fumarylacetoacetate and is inhibited by caspase inhibitors," *Proc. Natl. Acad. Sci. USA* 95:9552–9557 (Aug. 1998).

Lepschy, J., "Acylierung von Oxazolinonen–(5) unter besonderer Berücksichtigung der Dakin–West–Reaktion trifunktioneller Aminosäuren," *Ph.D. Thesis*, Technischen Universität München (1971).

Lieberthal, W. et al., "Necrosis and Apoptosis in Acute Renal Failure," *Sem. Nephr.* 18:505–518 (Sep. 1998).

Mattson, M.P. et al., "Amyloid β–peptide induces apoptosis–related events in synapses and dendrites," *Brain Res.* 807:167–176 (Oct. 1998).

Maulik, N. et al., "Oxidative stress developed during the reperfusion of ischemic myocardium induces apoptosis," *Free Rad. Biol. & Med.* 24:869–875 (Mar. 1998).

Miller, P.E. et al., "Photoreceptor cell death by apoptosis in dogs with sudden acquired retinal degeneration syndrome," *Am. J. Vet. Res.* 59:149–152 (Feb. 1998).

Miura, M. et al., "Induction of Apoptosis in Fibroblasts by IL–1β–Converting Enzyme, a Mammalian Homolog of the C. elegans Cell Death Gene ced–3," *Cell* 75:653–660 (1993).

Mosley, B. et al., "The Interleukin–1 Receptor Binds the Human Interleukin–1α Precursor but Not the Interleukin–1β Precursor," *J. Biol. Chem.* 262:2941–2944 (1987).

Mundle, S. D. et al., "Evidence for Involvement of Tumor Necrosis Factor–α in Apoptotic Death of Bone Marrow Cells in Myelodysplastic Syndromes," *Am. J. Hemat.* 60:36–47 (Jan. 1999).

Oppenheim, J. J. et al., "There is more than one interleukin 1," *Immun. Today* 7:45–56 (1986).

Ortiz, A. et al., "Cyclosporine A induces apoptosis in murine tubular epithelial cells: Role of caspases." *Kidney Int'l* 54:S–25–S–29 (Dec. 1998).

Rasnick, D., "Synthesis of Peptide Fluoromethyl Ketones and the Inhibition of Human Cathepsin B," *Anal. Biochem.* 149:461–465 (1985).

Rauber, P. et al., "The synthesis of peptidylfluoromethanes and their properties as inhibitors of serine proteinases and cysteine proteinases," *Biochem J.* 239:633–640 (1986).

Revesz, L. et al., "Synthesis of P1 Aspartate–Based Peptide Acyloxymethyl and Fluoromethyl Ketones as Inhibitors of Interleukin–1β–Converting Enzyme," *Tet. Lett.* 35:9693–9696 (1994).

Rich, D.H., "Inhibitors of aspartic proteinases," in *Proteinase inhibitors. Research monographs in cell and tissue physiology. vol. 12*, Barrett, A.J. and G. Salvesen, eds., Elsevier, Amsterdam, Holland, pp. 179–208 (1986).

Richberg, M.H. et al., "Dead cells do tell tales," *Curr. Op. Plant Bio.* 1:480–485 (Dec. 1998).

Rodriguez, I. et al., "Systemic Injection of a Tripeptide Inhibits the Intracellular Activation of CPP32–like Proteases In Vivo and Fully Protects Mice against Fas–mediated Fulminant Liver Destruction and Death," *J. Exp. Med.* 184:2067–2072 (1996).

Shaw, E., "Peptidyl fluoromethyl ketones as thiol protease inhibitors," *Biomed. Biochim. Acta* 45:1397–1403 (1986).

Sheikh, M.S. et al., "Ultraviolet–irridiation–induced apoptosis is mediated via ligand independent activation of tumor necrosis factor receptor 1," *Oncogene* 17:2555–2563 (Nov. 1998).

Sleath, P.R. et al., "Substrate Specificity of the Protease That Pocesses Human Intereukin–1β," *J. Bio. Chem.* 265:14526–14528 (1990).

Slomiany, B.L. et al., "Activation of Apoptotic Caspase–3 and Nitric Oxide Synthase–2 in Buccal Mucosa with Chronic Alcohol Ingestion," *Biochem. & Mol. Bio. Int'l.* 45:1199–1209 (Sep. 1998).

Steinberg, D., "Caspase Inhibitors. Molecules sought for treatment of diverse disorders," *Gen. Eng. News* 18:16,38,51 (Jul. 1998).

Suzuki, A., "The Dominant Role of CPP32 Subfamily in Fas–Mediated Hepatitis," *Proc. Soc. Exp. Biol. Med.* 217:450–454 (Apr. 1998).

Thornberry, N.A. et al., "A novel heterodimeric cysteine protease is required for interleukin–1β processing in monocytes," *Nature* 356:768–774 (1992).

Thornberry, N.A. et al., "A Combinatorial Approach Defines Specificities of Members of the Caspase Family and Granzyme B," *J. Biol. Chem.* 272:17907–17911 (1997).

Thornberry, N.A., "Caspases: key mediators of apoptosis," *Chem. & Bio.* 5:R97–R103 (May 1998).

Yuan, J. et al., "The C. elegans Cell Death Gene ced–3 Encodes a Protein Similar to Mammalian Interleukin–1β–Converting Enzyme," *Cell* 75:641–652 (1993).

Xue, D. et al., "The time course for infarction in a rat model of transit focal ischemia," *Stroke* 21:166, Abstract No. 36 (1990).

An, S. and Knox, K.A., "Ligation of CD40 rescues Ramos–Burkitt Lymphoma B cells from calcium ionophore– and antigen receptor–triggered apoptosis by inhibiting activation of the cysteine protease CPP32/Yama and cleavage of its substrate PARP," *FEBS Lett.* 386:115–122 (1996).

Hara, H. et al., "Inhibition of interleukin 1β converting enzyme family proteases reduces ischemic and excitatoxic neuronal damage," *Proc. Natl. Acad. Sci. USA* 94:2007–2012 (Mar. 1997).

Lotem, J. and Sachs, L., "Differential suppression by protease inhibitors and cytokines of apoptosis induced by wild–type p53 and cytotoxic agents," *Proc. Natl. Acad. Sci. USA* 93:12507–12512 (1996).

Weil, M. et al., "Is programmed cell death required for neural tube closure?" *Curr. Biol.* 7:281–284 (Apr. 1997).

International Search Report for International Application No. PCT/US99/05729, mailed Jul. 7, 1999.

Hotchkiss, R.S. et al., "Prevention of lymphocyte cell death in sepsis improves survival in mice," *PNAS* 96: 14541–14546 (Dec. 1999).

Jaeschke, H. et al., "Activation of Caspase 3 (CPP32)–Like Proteases Is Essential for TNF–α–Induced Hepatic Parenchymal Cell Apoptosis and Neutrophil–Mediated Necrosis in a Murine Endotoxin Shock Model," *J. Immunol.* 160:3480–3486 (1998).

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 1

Ala Tyr Val His Asp
 1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: peptide

<400> SEQUENCE: 2

Asp Glu Val Asp
```

DIPEPTIDE CASPASE INHIBITORS AND THE USE THEREOF

CROSS-REFERENCE TO RELATED APPLICATIONS

This application claims the benefit of U.S. application Ser. No. 60/078,051, filed Mar. 16, 1998, abandoned.

BACKGROUND OF THE INVENTION

1. Field of the Invention

This invention is in the field of medicinal chemistry. In particular, the invention relates to dipeptides which are potent inhibitors of caspases. The invention also relates to the use of these dipeptides for reducing or treating apoptotic cell death and/or reducing interleukin 1-β production.

2. Description of Background Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis et al., *Dev.* 112:591–603 (1991); Vaux et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995)).

Apoptosis is achieved through an endogenous mechanism of cellular suicide (Wyllie, A.H., in *Cell Death in Biology and Pathology*, Bowen and Lockshin, eds., Chapman and Hall (1981), pp. 9–34). A cell activates its internally encoded suicide program as a result of either internal or external signals. The suicide program is executed through the activation of a carefully regulated genetic program (Wylie et al., *Int. Rev. Cyt.* 68: 251 (1980); Ellis et al., *Ann. Rev. Cell Bio.* 7: 663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995)).

Mammalian interleukin-1β (IL-1β) plays an important role in various pathologic processes, including chronic and acute inflammation and autoimmune diseases (Oppenheim, J.H. et. al. *Immunology Today*, 7, 45–56 (1986)). IL-1 is synthesized as a cell associated precursor polypeptide (pro-IL-1) that is unable to bind IL-1 receptors and is biologically inactive (Mosley et al., *J. Biol. Chem.* 262:2941–2944 (1987)). By inhibiting conversion of precursor IL-1β to mature IL-1β, the activity of interleukin-1 can be inhibited. Interleukin-1β converting enzyme (ICE) is a protease responsible for the activation of interleukin-1β(IL-1β) (Thornberry, N.A., et al., *Nature* 356: 768 (1992); Yuan, J., et al., *Cell* 75: 641 (1993)). ICE is a substrate-specific cysteine protease that cleaves the inactive prointerleukin-1 to produce the mature IL-1. The genes that encode for ICE and CPP32 are members of the mammalian ICE/Ced-3 family of genes which presently includes at least twelve members: ICE, CPP32/Yama/Apopain, mICE2, ICE4, ICH1, TX/ICH-2, MCH2, MCH3, MCH4, FLICE/MACH/MCH5, ICE-LAP6 and $ICE_{rel}III$. The proteolytic activity of this family of cysteine proteases, whose active site (a cysteine residue) is essential for ICE-mediated apoptosis, appears critical in mediating cell death (Miura et al, *Cell* 75: 653–660 (1993)). This gene family has recently been named caspases (Alnernri, E.S. et. al. *Cell*, 87, 171 (1996) and Thornberry, N.A. et. al. *J. Biol. Chem.* 272, 17907–17911 (1997)) and divided into three groups according to its known functions. Table I summarized these known caspases.

TABLE I

| Enzyme* |
| --- |
| Group I: mediators of inflammation |
| caspase-1 (ICE) |
| caspase-4 $ICE_{rel}$-II TX, ICH-2 |
| caspase-5 ($ICE_{rel}$-III, TY) |
| Group II: effectors of apoptosis |
| caspase-2 (ICH-1, mNEDD2) |
| caspase-3 (apopain, CPP-32, YAMA) |
| cas ase-7. Mch-3 ICE-LAP3 CMH-1 |
| Group III: activators of apoptosis |
| caspase-6 (Mch2) |
| caspase-8 (MACH, FLICE, Mch5) |
| caspase-9 (ICE-LAP6, Mch6) |
| Caspase-10 |

IL-1 is also a cytokine involved in mediating a wide range of biological responses including inflammation, septic shock, wound healing, hematopoiesis and growth of certain leukemias (Dinarello, C.A., *Blood* 77:1627–1652 (1991); diGiovine et al., *Immunology Today* 11:13 (1990)).

Many potent caspase inhibitors have been prepared based on the peptide substrate structures of caspases. However, in contrast to their potency in vitro, no inhibitors with good efficacy ($IC_{50}$<1 M) in whole-cell models of apoptosis have been reported (Thornberry, N.A. *Chem. Biol.* 5:R97–103 (1998)). Therefore the need exists for cell death inhibitors that are efficacy in whole-cell models of apoptosis and active in animal model of apoptosis. These inhibitors thus can be employed as therapeutic agents to treat disease states in which regulated cell death and the cytokine activity of IL-1 play a role.

WO 93/05071 discloses peptide ICE inhibitors with the formula:

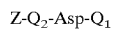

wherein Z is an N-terminal protecting group; $Q_2$ is 0 to 4 amino acids such that the sequence $Q_2$-Asp corresponds to at least a portion of the sequence Ala-Tyr-Val-His-Asp (SEQ ID NO:1); $Q_1$ comprises an electronegative leaving group. Exemplary dipeptides are Boc-His-Asp-$CH_2F$, Boc-Tyr-Asp-$CH_2F$, Boc-Phe-Asp-$CH_2F$, Ac-His-Asp-$CH_2F$, Ac-Tyr-Asp-$CH_2F$, Ac-Phe-Asp-$CH_2F$, Cbz-His-Asp-$CH_2F$, Cbz-Tyr-Asp-$CH_2F$ and Cbz-Phe-Asp-$CH_2F$.

WO 96/03982 discloses aspartic acid analogs as ICE inhibitors with the formula:

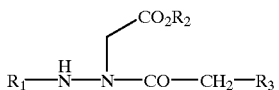

wherein $R_2$ is H or alkyl; $R_3$ is a leaving group such as halogen; $R_1$ is heteroaryl-CO or an amino acid residue.

U.S. Pat. No. 5,585,357 discloses peptidic ketones as ICE inhibitors with the formula:

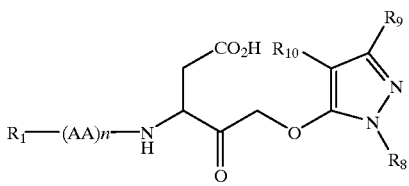

wherein n is 0–2; each AA is independently L-valine or L-alanine; $R_1$ is selected from the group consisting of N-benzyloxycarbonyl and other groups; $R_8$, $R_9$, $R_{10}$ are each independently hydrogen, lower alkyl and other groups.

Revesz et al. (*Tetrahedron Lett.* 35, 9693–9696, 1994) report the preparation of ethyl ester tripeptide:

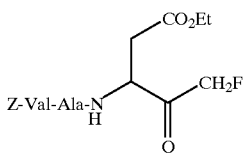

as a prodrug of the corresponding acid which is a potent ICE inhibitor.

SUMMARY OF THE INVENTION

The invention relates to dipeptides of formula I:

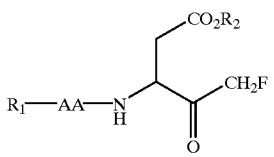

wherein $R_1$ is an N-terminal protecting group; AA is a residue of a non-natural -amino acid or -amino acid; $R_2$ is an optionally substituted alkyl or H.

The invention relates to the discovery that the compounds represented by Formula I are potent inhibitors of caspases. The invention also relates to the use of the dipeptides of the invention for reducing, preventing or treating maladies in which apoptotic cell death is either a causative factor or a result. Examples of uses for the present invention include protecting the nervous system following focal ischemia and global ischemia; treating neurodegenerative disorders such as Alzheimer's disease, Huntington's Disease, prion diseases, Parkinson's Disease, multiple sclerosis, amyotrophic lateral sclerosis, ataxia, telangiectasia, and spinobulbar atrophy; treating heart disease including myocardial infarction, congestive heart failure and cardiomyopathy; treating retinal disorders; treating autoimmune disorders including lupus erythematosus, rheumatoid arthritis, type I diabetes, Sjögren's syndrome and glomerulonephritis; treating polycystic kidney disease and anemia/erythropoiesis; treating immune system disorders, including AIDS and SCIDS; reducing or preventing cell, tissue and organ damage during transplantation; reducing or preventing cell line death in industrial biotechnology; reducing or preventing alopecia (hair loss); and reducing the premature death of skin cells.

The present invention provides pharmaceutical compositions comprising a compound of Formula I in an effective amount to reduce apoptotic cell death in an animal.

The present invention also provides preservation or storage solutions for mammalian organs or tissue, or growth media for mammalian or yeast cells, wherein an effective amount of a compound of Formula I is included in said solutions or media in order to reduce apoptotic cell death in said organs, tissue or cells.

DETAILED DESCRIPTION OF THE INVENTION

The inhibitors of caspases and apoptotic cell death of the present invention are compounds having the general Formula I:

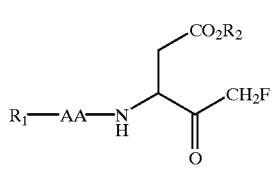

or pharmaceutically acceptable salts or prodrugs thereof, wherein:

$R_1$ is an N-terminal protecting group including t-butyloxycarbonyl, acetyl, and benzyloxycarbonyl; AA is a residue of a non-natural -amino acid. $R_2$ is an optionally substituted alkyl or H.

With respect to $R_2$, preferred alkyl groups are $C_{1-6}$ alkyl groups, e.g. methyl, ethyl, propyl, isopropyl, isobutyl, pentyl and hexyl groups; and substituted $C_{1-6}$ alkyl groups, e.g. $CH_2OCH_3$ and $CH_2OCOCH_3$ (AM).

The invention relates to the discovery that the compounds represented by Formula I are potent inhibitors of caspases. These inhibitors slow or block cell death in a variety of clinical conditions and industrial applications in which the loss of cells, tissues or entire organs occurs. Therefore, the invention is also related to methods of treating, preventing or reducing conditions in which apoptosis plays a role. These conditions are more fully described below.

The methods comprise administering to an animal in need of such treatment an inhibitor of the present invention, or a pharmaceutically acceptable salt or prodrug thereof, in an amount effective to inhibit apoptotic cell death.

Preferred embodiments of the compounds of Formula I that may be employed as inhibitors of caspases are represented by Formula II:

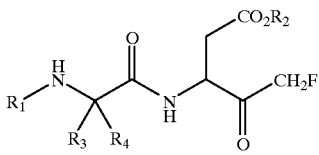

II or pharmaceutically acceptable salts or prodrugs thereof wherein $R_1$ and $R_2$ are as defined previously with respect to Formula I; and $R_3$ and $R_4$ independently are haloalkyl, aryl, heterocyclic, heteroaryl, $C_{1-10}$ alkyl, alkenyl, alkynyl, aralkyl, aralkenyl, aralkynyl and hydroxyalkyl.

Preferred $R_1$ is t-butyloxycarbonyl, acetyl or benzyloxycarbonyl. Preferred $R_2$ is H, Me, Et, t-Bu or AM. Preferred $R_3$ is $C_{1-10}$ alky, haloalkyl, aryl or heteroaryl, and preferred $R_4$ is Me.

Another preferred embodiment of the compounds of Formula I that may be employed as inhibitors of caspases are represented by Formula III:

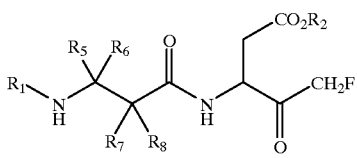

III or pharmaceutically acceptable salts or prodrugs thereof wherein $R_1$ and $R_2$ are as defined previously with respect to Formula I; and $R_5$, $R_6$, $R_7$ and $R_8$ independently are hydrogen, haloalkyl, aryl, heterocyclic, carbocyclic, heteroaryl, $C_{1-10}$ alkyl, alkenyl, alkynyl, aralkyl, aralkenyl, aralkynyl or hydroxyalkyl; provided that at least one of the $R_5$–$R_8$ is other than hydrogen.

Preferred $R_1$ is t-butyloxycarbonyl, acetyl or benzyloxycarbonyl. Preferred $R_2$ is H, Me, Et, t-Bu or AM. Preferred $R_5$ is hydrogen, $C_{1-10}$ alkyl, haloalkyl, aryl or heteroaryl; preferred $R_6$ is hydrogen or Me. Preferred $R_7$ is $C_{1-10}$ alkyl, haloalkyl, aryl or heteroaryl; preferred $R_8$ is hydrogen or Me.

Another preferred embodiment of the compounds of Formula I that may be employed as inhibitors of caspases are represented by Formula IV:

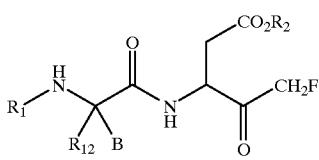

IV or pharmaceutically acceptable salts or prodrugs thereof wherein $R_1$ and $R_2$ are as defined previously with respect to Formula I; and $R_{12}$ is hydrogen or $C_{1-10}$ alkyl; B is aryl, heteroaryl, saturated or partially unsaturated carbocycle or saturated or partially unsaturated heterocycle, any of which is optionally substituted by one or more groups selected from hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, cyano, $C_1$–$C_6$ acylamino, hydroxy, $C_1$–$C_6$ acyloxy, $C_1$–$C_6$ alkoxy, alkylthio, or carboxy.

Preferred $R_1$ is t-butyloxycarbonyl, acetyl or benzyloxycarbonyl. Preferred $R_2$ is H, Me, Et, t-Bu or AM. Preferred $R_{12}$ is hydrogen, or Me. Preferred B is optionally substituted phenyl, thienyl, furyl, pyridyl, cyclohexyl, cyclopentyl, cyclobutyl or cyclopropyl.

Other preferred embodiments of the compounds of Formula I that may be employed as inhibitors of caspases are represented by Formula V:

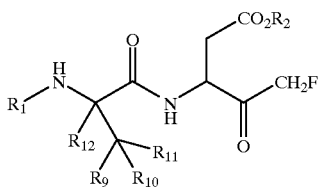

V or pharmaceutically acceptable salts or prodrugs thereof wherein $R_1$, $R_2$ and $R_{12}$ are as defined previously with respect to Formula I and IV; and $R_9$, $R_{10}$ and $R_{11}$ independently are hydrogen, $C_{1-10}$ alkyl, halogen, haloalkyl, optionally substituted aryl, heteroaryl, saturated or partially unsaturated carbocycle or saturated or partially unsaturated heterocycle; provided that at least one of $R_9$–$R_{11}$ is halogen, haloalkyl, heteroaryl, saturated or partially unsaturated carbocycle or saturated or partially unsaturated heterocycle.

Preferred $R_1$ is t-butyloxycarbonyl, acetyl or benzyloxycarbonyl. Preferred $R_2$ is H, Me, Et, t-Bu or AM. Preferred $R_{12}$ is hydrogen, or Me. Preferred $R_9$, $R_{10}$ and $R_{11}$ independently are hydrogen, methyl, chloro, fluoro, fluoromethyl, difluoromethyl, trifluoromethyl, chloromethyl, chlorofluoromethyl, thienyl, furyl, pyridyl, cyclohexyl, cyclopentyl, cyclobutyl and cyclopropyl.

Exemplary preferred inhibitors of caspases and apoptosis having Formula I include, without limitation:

Boc-Phg-Asp-fmk,
Boc-(2-F-Phg)-Asp-fmk,
Boc-($F_3$-Val)-Asp-fmk,
Boc-(3-F-Val)-Asp-fmk,
Ac-Phg-Asp-fmk,
Ac-(2-F-Phg)-Asp-fmk,
Ac-($F_3$-Val)-Asp-fmk,
Ac-(3-F-Val)-Asp-fmk,
Z-Phg-Asp-fmk,
Z-(2-F-Phg)-Asp-fmk,
Z-($F_3$-Val)-Asp-fmk,
Z-Chg-Asp-fmk,
Z-(2-Fug)-Asp-fmk,
Z-(4-F-Phg)-Asp-fmk,
Z-(4-Cl-Phg)-Asp-fmk,
Z-(3-Thg)-Asp-fmk,
Z-(2-Fua)-Asp-fmk,
Z-(2-Tha)-Asp-fmk,
Z-(3-Fua)-Asp-fmk,
Z-(3-Tha)-Asp-fmk,
Z-(3-Cl-Ala)-Asp-fmk,
Z-(3-F-Ala)-Asp-fmk,
Z-($F_3$-Ala)-Asp-fmk,
Z-(3-F-3-Me-Ala)-Asp-fmk,
Z-(3-Cl-3-F-Ala)-Asp-fmk,
Z-(2-Me-Val)-Asp-fmk,
Z-(2-Me-Ala)-Asp-fmk,
Z-(2-i-Pr-β-Ala)-Asp-fmk, Z-(3-Ph-β-Ala)-Asp-fmk,
Z-(3-CN-Ala)-Asp-fmk,
Z-(1-Nal)-Asp-fmk,
Z-Cha-Asp-fmk,
Z-(3-CF$_3$-Ala)-Asp-fmk,
Z-(4-CF$_3$-Phg)-Asp-fmk,
Z-(3-Me$_2$N-Ala)-Asp-fmk,
Z-(2-Abu)-Asp-fmk,
Z-Tle-Asp-fmk,
Z-Cpg-Asp-fmk,
Z-Cbg-Asp-fmk,
Z-Thz-Asp-fmk,
Z-(3-F-Val)-Asp-fmk, and
Z-(2-Thg)-Asp-fmk.

Where Z is benzyloxycarbonyl, BOC is tert.-butoxycarbonyl, Ac is acetyl, Phg is phenylglycine, 2-F-Phg is (2-fluorophenyl)glycine, F$_3$-Val is 4,4,4-trifluoro-valine, 3-F-Val is 3-fluoro-valine, 2-Thg is (2-thienyl)glycine, Chg is cyclohexylglycine, 2-Fug is (2-furyl)glycine, 4-F-Phg is (4-fluorophenyl)glycine, 4-Cl-Phg is (4-chlorophenyl)glycine, 3-Thg is (3-thienyl)glycine, 2-Fua is (2-furyl)alanine, 2-Tha is (2-thienyl)alanine, 3-Fua is (3-furyl)alanine, 3-Tha is (3-thienyl)alanine, 3-Cl-Ala is 3-chloroalanine, 3-F-Ala is 3-fluoroalanine, F$_3$-Ala is 3,3,3-trifluoroalanine, 3-F-3-Me-Ala is 3-fluoro-3-methylalanine, 3-Cl-3-F-Ala is 3-chloro-3-fluoroalanine, 2-Me-Val is 2-methylvaline, 2-Me-Ala is 2-methylalanine, 2-i-Pr-β-Ala is 3-amino-2-isopropylpropionic acid, 3-Ph-β-Ala is 3-amino-3-phenylpropionic acid, 3-CN-Ala is 3-cyanoalanine, 1-Nal is 3-(1-naphthyl)-alanine, Cha is cyclohexylalanine, 3-CF$_3$-Ala is 2-amino-4,4,4-trifluorobutyric acid, 4-CF$_3$-Phg is 4-trifluoromethylphenylglycine, 3-Me$_2$N-Ala is 3-dimethylaminoalanine, 2-Abu is 2-aminobutyric acid, Tle is tert-leucine, Cpg is cyclopentylglycine, Cbg is cyclobutylglycine, and Thz is thioproline. These amino acid derivatives may be enantiomerically pure or racemic mixtures.

Useful aryl groups are C$_{6-14}$ aryl, especially C$_{6-10}$ aryl. Typical C$_{6-14}$ aryl groups include phenyl, naphthyl, phenanthrenyl, anthracenyl, indenyl, azulenyl, biphenyl, biphenylenyl and fluorenyl groups.

Useful cycloalkyl groups are C$_{3-8}$ cycloalkyl. Typical cycloalkyl groups include cyclopropyl, cyclobutyl, cyclopentyl and cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluoro, chloro, bromo and iodo.

Useful alkyl groups include straight-chained and branched C$_{1-10}$ alkyl groups, more preferably C$_{1-6}$ alkyl groups. Typical C$_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups are C$_{2-6}$ alkenyl groups, preferably C$_{2-4}$ alkenyl. Typical C$_{2-4}$ alkenyl groups include ethenyl, propenyl, isopropenyl, butenyl, and sec.-butenyl.

Useful alkynyl groups are C$_{2-6}$ alkynyl groups, preferably C$_{2-4}$ alkynyl. Typical C$_{2-4}$ alkynyl groups include ethynyl, propynyl, butynyl, and 2-butynyl groups.

Useful arylalkyl groups include any of the above-mentioned C$_{1-10}$ alkyl groups substituted by any of the above-mentioned C$_{6-14}$ aryl groups. Useful values include benzyl, phenethyl and naphthylmethyl.

Useful arylalkenyl groups include any of the above-mentioned C$_{2-4}$ alkenyl groups substituted by any of the above-mentioned C$_{6-14}$ aryl groups.

Useful arylalkynyl groups include any of the above-mentioned C$_{2-4}$ alkynyl groups substituted by any of the above-mentioned C$_{6-14}$ aryl groups. Useful values include phenylethynyl and phenylpropynyl.

Useful haloalkyl groups include C$_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl, chloromethyl, chlorofluoromethyl and trichloromethyl groups.

Useful hydroxyalkyl groups include C$_{1-10}$ alkyl groups substituted by hydroxy, e.g. hydroxymethyl, hydroxyethyl, hydroxypropyl and hydroxybutyl groups.

Useful alkoxy groups include oxygen substituted by one of the C$_{1-10}$ alkyl groups mentioned above.

Useful alkylthio groups include sulphur substituted by one of the C$_{1-10}$ alkyl groups mentioned above. Also included are the sulfoxides and sulfoxides of such alkylthio groups.

Useful acylamino groups are any C$_{1-6}$ acyl (alkanoyl) attached to an amino nitrogen, e.g. acetamido, propionamido, butanoylamido, pentanoylamido, hexanoylamido as well as aryl-substituted C$_{2-6}$ substituted acyl groups.

Useful acyloxy groups are any C$_{1-6}$ acyl (alkanoyl) attached to an oxy (—O—) group, e.g. acetoxy, propionoyloxy, butanoyloxy, pentanoyloxy, hexanoyloxy and the like.

Useful amino groups include —NH$_2$, —NHR$_{14}$, and —NR$_{14}$R$_{15}$, wherein R$_{14}$ and R$_{15}$ are C$_{1-10}$ alkyl or cycloalkyl groups as defined above.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl and pyrazolinyl groups.

Useful heteroaryl groups include any one of the following: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dionyl, 7-aminoisocoumarin-yl, pyrido[1,2-a]pyrimidin-4-onyl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Certain of the compounds of the present invention may exist as stereoisomers including optical isomers. The invention includes all stereoisomers and both the racemic mixtures of such stereoisomers as well as the individual entantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxide, Tris(hydroxymethyl) aminomethane (TRIS, tromethane) and glucosamine.

Examples of prodrugs include compounds of Formula I–V wherein $R_2$ is an alkyl group or substituted alkyl group such as $CH_2OCH_3$ and $CH_2OCOCH_3$ (AM ester). Further, in the cases where AA contains a carboxylic acid group, examples of prodrugs of Formula I–V wherein $R_2$ is H includes compounds in which either or both carboxyl groups are esterified (e.g. with a $C_{1-6}$ alcohol) or are in the form of the corresponding amides (e.g. with a $C_{1-6}$ amine). Other prodrugs of the compounds of the invention include $C_{1-6}$ esters, thioesters and amides of the compounds of the invention where one of the $R_3$, $R_4$, $R_7$, $R_8$, $R_{12}$ or B groups are substituted with a hydroxy, thio or amino group. It is anticipated that ester, thioester and amido derivatives will be more lipophilic than the parent compound, will be readily taken up by cells in vivo. It is also anticipated that the esters and thioesters will be cleaved in vivo by endogenous esterases to give the parent hydroxy- or mercapto-substituted compound.

The invention is also directed to a method for treating disorders responsive to the inhibition of apoptosis in animals suffering thereof. Particular preferred embodiments of compounds for use in the method of this invention are represented by previously defined Formula I–V.

The compounds of this invention may be prepared using methods known to those skilled in the art. Specifically, compounds with Formulae I–V can be prepared as illustrated by exemplary reactions in Scheme 1. The intermediate 1 was prepared according to Revesz et al. (*Tetrahedron Lett.* 35, 9693–9696, 1994). Coupling of 1 with a N-protected amino acid, which is either commercial available or which can be prepared from a commercial available compound, such as Z-phenylglycine-OH (Z-Phg-OH) gave amide 2. Oxidation of 2 by Dess-Martin reagent according to Revesz et al. (*Tetrahedron Lett.* 35, 9693–9696, 1994) gave 3 as a mixture of diasteriomers. Acid catalyzed cleavage of the ester gave the free acid 4.

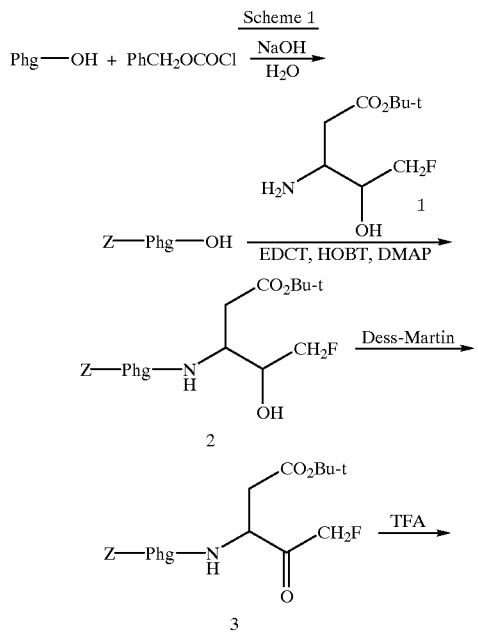

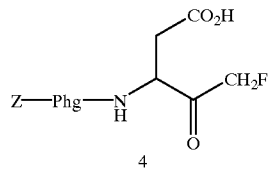

Other examples of non-natural amino acids that may be used in this process include, without limitation, the enantiomeric and racemic forms of 2-methylvaline, 2-methylalanine, (2-i-propyl)-β-alanine, phenylglycine, 4-methylphenylglycine, 4-isopropylphenylglycine, 3-bromophenylglycine, 4-bromophenylglycine, 4-chlorophenylglycine, 4-methoxyphenylglycine, 4-ethoxyphenylglycine, 4-hydroxyphenylglycine, 3-hydroxyphenylglycine, 3,4-dihydroxyphenylglycine, 3,5-dihydroxyphenylglycine, 2,5-dihydrophenylglycine, 2-fluorophenylglycine, 3-fluorophenylglycine, 4-fluorophenylglycine, 2,3-difluorophenylglycine, 2,4-difluorophenylglycine, 2,5-difluorophenylglycine, 2,6-difluorophenylglycine, 3,4-difluorophenylglycine, 3,5-difluorophenylglycine, 2-(trifluoromethyl)phenylglycine, 3-(trifluoromethyl)phenylglycine, 4-(trifluoromethyl) phenylglycine, 2-(2-thienyl)glycine, 2-(3-thienyl)glycine, 2-(2-furyl)glycine, 3-pyridylglycine, 4-fluorophenylalanine, 4-chlorophenylalanine, 2-bromophenylalanine, 3-bromophenylalanine, 4-bromophenylalanine, 2-naphthylalanine, 3-(2-quinoyl)alanine, 3-(9-anthracenyl) alanine, 2-amino-3-phenylbutanoic acid, 3-chlorophenylalanine, 3-(2-thienyl)alanine, 3-(3-thienyl) alanine, 3-phenylserine, 3-(2-pyridyl)serine, 3-(3-pyridyl) serine, 3-(4-pyridyl)serine, 3-(2-thienyl)serine, 3-(2-furyl) serine, 3-(2-thiazolyl)alanine, 3-(4-thiazolyl)alanine, 3-(1,2, 4-triazol-1-yl)-alanine, 3-(1,2,4-triazol-3-yl)-alanine, hexafluorovaline, 4,4,4-trifluorovaline, 3-fluorovaline, 5,5, 5-trifluoroleucine, 2-amino-4,4,4-trifluorobutyric acid, 3-chloroalanine, 3-fluoroalanine, 2-amino-3-flurobutyric acid, 3-fluoronorleucine, 4,4,4-trifluorothreonine, L-allylglycine, tert-Leucine, propargylglycine, vinylglycine, S-methylcysteine, cyclopentylglycine, cyclohexylglycine, 3-hydroxynorvaline, 4-azaleucine, 3-hydroxyleucine, 2-amino-3-hydroxy-3-methylbutanoic acid, 4-thiaisoleucine, acivicin, ibotenic acid, quisqalic acid, 2-indanylglycine, 2-aminoisobutyric acid, 2-cyclobutyl-2-phenylglycine, 2-isopropyl-2-phenylglycine, 2-methylvaline, 2,2-diphenylglycine, 1-amino-1-cyclopropanecarboxylic acid, 1-amino-1-cyclopentanecarboxylic acid, 1-amino-1-cyclohexanecarboxylic acid, 3-amino-4,4,4-trifluorobutyric acid, 3-phenylisoserine, 3-amino-2-hydroxy-5-methylhexanoic acid, 3-amino-2-hydroxy-4-phenylbutyric acid, 3-amino-3-(4-bromophenyl)propionic acid, 3-amino-3-(4-chlorophenyl)propionic acid, 3-amino-3-(4-methoxyphenyl)propionic acid, 3-amino-3-(4-fluorophenyl) propionic acid, 3-amino-3-(2-fluorophenyl)propionic acid, 3-amino-3-(4-nitrophenyl)propionic acid, and 3-amino-3-(1-naphthyl)propionic acid. These non-natural amino acids are commercial available from the following commercial suppliers including Aldrich, Sigma, Fluka, Lancaster, ICN, TCI, Advanced ChemTech, Oakwood Products, Indofine Chemical Company, NSC Technology, PCR Research Chemicals, Bachem, Acros Organics, Celgene, Bionet Research, Tyger Scientific, Tocris, Research Plus, Ash Stevens, Kanto, Chiroscience, and Peninsula Lab. The following amino acids can be synthesized according to literature procedures: 3,3,3-trifluoroalanine (Sakai, T.; et al.. *Tetrahedron* 1996, 52, 233) and 3,3-difluoroalanine (D'Orchymont, H. *Synthesis* 1993, 10, 961). Other N-protecting groups can be used in the place of Z include Acetyl (Ac), tert-butoxycarbonyl (Boc), methoxycarbonyl or ethoxycarbonyl.

An important aspect of the present invention is the discovery that compounds having Formulae I–V are potent inhibitors of caspases. Therefore, these inhibitors are expected to slow or block cell death in a variety of clinical conditions in which the loss of cells, tissues or entire organs occurs.

The cell death inhibitors of the present invention can be used to reduce or prevent cell death in the nervous system (brain, spinal cord, and peripheral nervous system) under various conditions of ischemia and excitotoxicity, including, but not limited to, focal ischemia due to stroke and global ischemia due to cardiac arrest, as well as spinal cord injury (Emery et al. *J. Neurosurgery,* 89: 911–920 (1998)). One particular usage is to treat the effects of oxygen deprivation which can occur during the birth of infants in high-risk labors or drowning. The cell death inhibitors can also be used to reduce or prevent cell death in the nervous system due to traumatic injury (such as head trauma), viral infection or radiation-induced nerve cell death (for example, as a side-effect of cancer radiotherapy). The cell death inhibitors can also be used to reduce or prevent cell death in a range of neurodegenerative disorders, including but not limited to Alzheimer's disease (Mattson et al. *Brain Res.* 807: 167–176 (1998)), Huntington's Disease, Parkinson's Disease, multiple sclerosis, amyotrophic lateral sclerosis, and spinobulbar atrophy. The in vivo neuroprotective properties of cell death inhibitors of the invention can be tested in a rat transient focal brain ischemia model (Xue et al., *Stroke* 21: 166 (1990)).

The cell death inhibitors of the invention can be used to reduce or prevent cell death in any condition which potentially results in the death of cardiac muscle (Black et al., *J. Mol. Cel. Card.* 30: 733–742 (1998) and Maulik et al. *Free Radic. Biol. Med.* 24: 869–875 (1998)). This includes myocardial infarction due to myocardial ischemia and reperfusion, congestive heart failure and cardiomyopathy. One particular application is to reduce or prevent myocardial cell death as occurs in certain viral infections of the heart.

The in vivo activity of the cell death inhibitors of the invention can be tested using the "mouse liver apoptosis" model described by Rodriguez et al. (Rodriguez et al., *J. Exp. Med.,* 184:2067–2072 (1996)). In this model, mice are treated intravenously (IV) with an antiFas antibody which induces massive apoptosis in the liver and other organs, leading to generalized organ failure and death. This model is useful for indirectly testing the systemic bioavailability of the cell death inhibitors of the invention, as well as their in vivo anti-apoptotic properties. The cell death inhibitors of the invention therefore can be used to reduce or prevent apoptosis of liver cells (Jones et al. *Hepatology* 27: 1632–42 (1998)) such as in sepsis (Jaeschke et al. *J. Immunol.* 160: 3480–3486 (1998)) and hereditary tyrosinemia type 1 (HT1) (Kubo et al. *Prov. Natl. Acad. Sci. USA,* 95: 9552–9557 (1998). The cell death inhibitors of the invention also can be used to treat hepatitis (Suzuki, *Proc. Soc. Exp. Biol. Med.* 217: 450–454 (1998)).

The cell death inhibitors of the invention can be used to reduce or prevent cell death of retinal neurons (Kermer et al. *J. Neurosci.* 18: 4656–4662 (1998) and Miller et al. *Am. J Vet. Res.* 59: 149–152 (1998)) as can occur in disorders which increase intraocular pressure (such as glaucoma) or retinal disorders associated with the aging process (such as age-related macular degeneration). The inhibitors can also be used to treat hereditary degenerative disorders of the retina, such as retinitis pigmentosa.

The cell death inhibitors of the invention can also be used to reduce or prevent cell death in the kidney. This includes renal amyloidosis (Hiraoka et al. *Nippon Jinzo Gakkai Shi,* 40: 276–83 (1998)), acute renal failure (Lieberthal et al. *Semin Nephrol.* 18: 505–518 (1998)), murine tubular epithelial cell death induced by cyclosporine A (Ortiz et al. *Kidney International Supp.* 68: S25–S29 (1998)) and HIV-induced nephropathy (Conaldi et al. *J. Clin. Invest.* 102: 2041–2049 (1998)).

The cell death inhibitors of the invention can also be used to reduce or prevent cell death of buccal mucosa due to chronic alcohol ingestion (Slomiany et al. *Biochem. Mol. Biol. Int.* 45: 1199–1209 (1998)).

The cell death inhibitors of the invention can also be used to reduce or prevent cell death in plants (Richberg et al. *Curr. Opin. Plant Biol.* 1: 480–485 (1998)), such as plant cell death due to pathogens (Pozo et al. *Curr. Biol* 8: 1129–1132 (1998) and Greenberg et al. *Cell,* 77: 551–563 (1994)).

The cell death inhibitors of the invention can also be used to reduce or prevent cell death due to radiation and ultraviolet-irradiation (Sheikh et al. *Oncogene,* 17: 2555–2563 (1998)).

The cell death inhibitors of the invention can also be used to reduce or prevent apoptotic death of bone marrow cells in myelodysplastic syndromes (MDS) (Mundle et al., *Am. J. Hematol.* 60: 36–47 (1999)).

The cell death inhibitors of the invention can also be used to reduce or prevent premature death of cells of the immune system, and are particularly useful in treating immune deficiency disorders, such as acquired immune deficiency syndrome (AIDS), severe combined immune deficiency syndrome (SCIDS) and related diseases. The cell death inhibitors can also be used to treat radiation-induced immune suppression.

Transplantation of human organs and tissues is a common treatment for organ failure. However, during the transplantation process, the donor organ or tissue is at risk for cell death since it is deprived of its normal blood supply prior to being implanted in the host. This ischemic state can be treated with cell death inhibitors by infusion into the donor organ or tissue, or by direct addition of the cell death inhibitors to the organ/tissue storage medium. Cell death inhibitors may also be used to reduce or prevent cell death in the donor organ/tissue after it has been transplanted to protect it from the effects of host immune cells which kill their targets by triggering apoptosis. The cytoprotective effects of cell death inhibitors can also be used to prevent the death of human or animal sperm and eggs used in in vitro fertilization procedures. These inhibitors can be used during the harvesting process and can also be included in the storage medium.

Mammalian cell lines, insect cells and yeast cells are commonly used to produce large amounts of recombinant proteins (such as antibodies, enzymes or hormones) for industrial or medicinal use. The lifespan of some of these cell lines is limited due to growth conditions, the nature of the recombinant molecule being expressed (some are toxic) and other unknown factors. The lifespans of industrial cell lines can be extended by including these cell death inhibitors in the growth medium in a concentration range of 1–100 M.

The factors governing hair growth and loss are largely unknown. There is some evidence, however, that hair follicle regression (referred to as catagen) may be due at least partially to apoptosis. Therefore, it is contemplated that the cell death inhibitors of the present invention can be used to treat hair loss that occurs due to various conditions, including but not limited to male-pattern baldness, radiation-induced or chemotherapy-induced hair loss, and hair loss due to emotional stress. There is also evidence that apoptosis may play a role in the loss of hair color. Therefore, it is contemplated that the cell death inhibitors of the present invention can also be used in treating or preventing cases of premature graying of the hair.

The death of skin epithelial cells can occur after exposure to high levels of radiation, heat or chemicals. It is contemplated that the cell death inhibitors of the present invention can be used to treat, reduce or prevent this type of skin damage. In one particular application, the cell death inhibitors can be applied as part of a topical formulation, e.g. an ointment, to treat acute over-exposure to the sun and to prevent blistering and peeling of the skin.

Goldberg et al. (*Nature Genetics* 13: 442–449 (1996)) reported recently that huntingtin, a protein product of Huntington's disease (HD) gene, can be cleaved by CPP32 but not ICE. The mutation underlying HD is an expansion of a CAG trinucleotide at the 5' end of the HD gene. The trinucleotide expansion exceeding 36 repeats is associated with the clinical presentation of HD. The CAG expansion promotes cleavage of huntingtin by CPP32, thus links the role of CPP32 in the apoptotic cell death in HD. Compounds of the present invention with CPP32 inhibiting activity will be useful in blocking CPP32 induced apoptotic cell death, thus in preventing and treating HD and other disorders characterized by expansion of trinucleotide repeats such as myotonic dystrophy, fragile X mental retardation, spinobulbar muscular atrophy, spinocerebellar atoxia type I and Dentato-Rubro pallidoluysian atrophy.

Compositions within the scope of this invention include all compositions wherein the compounds of the present invention are contained in an amount which is effective to achieve its intended purpose. While individual needs vary, determination of optimal ranges of effective amounts of each component is with the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for apoptosis-mediated disorders, e.g., neuronal cell death, heart disease, retinal disorders, polycystic kidney disease, and immune system disorders. Preferably, about 0.01 to about 10 mg/kg is orally administered to treat or prevent such disorders. For intramuscular injection, the dose is generally about one-half of the oral dose. For example, for treatment or prevention of neuronal cell death, a suitable intramuscular dose would be about 0.0025 to about 25 mg/kg, and most preferably, from about 0.01 to about 5 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular cell death inhibitors of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular cell death inhibitors of the present invention with a solution of a pharmaceutically acceptable non-toxic base such as sodium hydroxide, potassium hydroxide, choline hydroxide, sodium carbonate Tris and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin damage, such as that caused by exposure to high levels of radiation, including ultraviolet radiation, heat or chemicals.

One or more additional substances which have therapeutic effects on the skin may also be incorporated in the compositions. Thus, the composition may also contain one or more compounds capable of increasing cyclic-AMP levels in the skin. Suitable compounds include adenosine or a nucleic acid hydrolysate in an amount of about 0.1–1% and papaverine, in an amount of about 0.5–5%, both by weight based on the weight of the composition. Also suitable are β-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the compositions of this invention include any compounds known to have a beneficial effect on skin. Such compounds include retinoids such as Vitamin A, in an amount of about 0.003–0.3% by weight and chromanols such as Vitamin E or a derivative thereof in an amount of about 0.1–10% by weight, both based on the weight of the composition. Additionally, anti-inflammatory agents and keratoplastic agents may be incorporated in the cosmetic composition. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent is coal tar in an amount of about 0.1–20% or anthralin in an amount of about 0.05–2% by weight, both based on the weight of the composition.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

In addition, these compositions may include other medicinal agents, growth factors, wound sealants, carriers, etc., that are known or apparent to those skilled in the art. The compositions of the invention are administered to a warm-blooded animal, such as human, already suffering from a skin damage, such as a burn, in an amount sufficient to allow the healing process to proceed more quickly than if the host were not treated. Amounts effective for this use will depend on the severity of the skin damage and the general state of health of the patient being treated. Maintenance dosages over a prolonged period of time may be adjusted as necessary. For veterinary uses, higher levels may be administered as necessary.

In the case of an animal suffering from decreased hair growth, the compositions of the invention are administered in an amount sufficient to increase the rate of hair growth. Amounts effective for this use will depend on the extent of decreased hair growth, and the general state of health of the patient being treated. Maintenance dosages over a prolonged period of time may be adjusted as necessary. For veterinary uses, higher levels may be administered as necessary.

When the compounds are to be administered to plants, they may be applied to the leaves and/or stems and/or flowers of the plant, e.g. by spraying. The compounds may be spayed in particulate form or dissolved or suspended in an appropriate carrier, e.g. in water or an oil-water emulsion. The compounds may also be combined with the soil of the plant. In this embodiment, the compounds are taken up by the roots of the plant.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Z-[(S)-Phg]-Asp-fmk

Step A. Z-(S)-Phenylglycine. To a solution of (S)-(+)-phenylglycine (2.0 g, 13.2 mmol) in 2 N NaOH aqueous solution (30 mL) was added benzyl chloroformate (2.3 mL, 16.2 mmol) at room temperature. The resulting solution was stirred at room temperature for 5 h, and acidified to pH=1. The resulting white solid was collected by filtration, washed with water and dried in vacuo to yield the title compound (2.5 g, 8.8 mmol, 67%). $^1$H NMR (CDCl$_3$): δ 8.05 (d, J=8.4, 1H), 7.40–7.28 (m, 10H), 5.12 (d, J=8.4, 1H), 5.03 (s, 2H).

Step B. tert-Butyl 5-fluoro-3-[Z-(S)-phenyl-Gly-amido]-4-hydroxypentanoate. To a solution of Z-(S)-phenylglycine (205 mg, 0.72 mmol) in THF (10 mL) was added 1-(2-dimethylaminopropyl)-3-ethylcarbodiimide (EDCI) (148 mg, 0.77 mmol), 1-hydroxybenzotriazole hydrate (HOBT) (112 mg, 0.73 mmol) and dimethylaminopyridine (DMAP) (61 mg, 0.50 mmol). The resulting mixture was stirred at rt for 5 min, to which was then added a solution of tert-butyl 3-amino-5-fluoro-4-hydroxypentanoate (98 mg, 0.47 mmol) in THF (5 mL). The resulting mixture was stirred at rt for three days. The THF was evaporated in vacuo to give a residue, which was dissolved in 50 mL of ethyl acetate. The solution was washed with 2N HCl, saturated NaHCO$_3$, brine, dried over Na$_2$SO$_4$, concentrated in vacuo and the residue was purified by flash chromatography (EtOAc/Hexane 6/5) to give the title compound as a colorless oil (200 mg, 0.42 mmol, 90%). $^1$H NMR (CDCl$_3$): δ 7.36–7.26 (m, 10H), 6.74–6.49 (m, 1H), 5.98 (m, 1H), 5.14–5.02 (m, 3H), 4.50–3.91 (m, 4H), 2.68–2.51 (m, 2H), 1.41–1.33 (m, 9H).

Step C. Z-[(S)-Phg]-Asp(To-Bu)-fmk. To a suspension of Dess-Martin periodinane (0.67 g, 1.59 mmol) in dichloromethane (15 mL) was added a solution of tert-butyl 5-fluoro-3-(Z-phenyl-Gly-amido)-4-hydroxypentanoate (150 mg, 0.32 mmol) in dichloromethane (5 mL). The mixture was refluxed for 20 h, cooled to rt, and 25 mL of saturated sodium bicarbonate aqueous solution containing 1.0 g of Na$_2$S$_2$O$_3$ was added. The resulting mixture was stirred for 1 h, extracted with 1:1 hexane/EtOAc (3×25 mL). The combined organic phase was washed with water and brine, dried over Na$_2$SO$_4$ and concentrated in vacuo to yield the title compound as a hydroscopic white solid (140 mg, 0.30 mmol, 94%). $^1$H NMR (CDCl$_3$): δ 7.37–7.31 (m, 10H), 6.84 (d, J=6.9, 1H), 6.03–5.96 (m, 1H), 5.23–4.65 (m, 6H), 3.03–2.58 (m, 2H), 1.40, 1.29 (2s, 9H).

Step D. Z-[(S)-Phg]-Asp-fmk. To a solution of Z-[(S)-Phg]-Asp(To-Bu)-fmk (140 mg, 0.30 mmol) in 5 mL of CH$_2$Cl$_2$ was added 1 mL of TFA. The resulting solution was allowed to stir at rt for 1 h. The solvent was evaporated in vacuo to give a residue, which was purified by flash chromatography (acetone) to give the title compound as a white solid (110 mg, 0.26 mmol, 87%). $^1$H NMR (DMSO-d$_6$): δ 8.80 (m, 1H), 8.00 (s, 1H), 7.97–7.67 (m, 1H), 7.47–7.20 (m, 10H), 5.26–4.94 (m, 2H), 5.03 (s, 2H), 4.54 (s, 1H), 2.68–2.56 (m, 2H).

EXAMPLE 2

Z-(2-Me-Val)-Asp-fmk

The title compound was prepared from DL-2-methylvaline in four-steps as described in Example 1. $^1$H NMR (DMSO-d$_6$): δ 8.00 (brs, 1H), 7.35 (s, 5H), 4.99 (s, 2H), 5.10–4.53 (m, 3H), 2.88–2.48 (m, 2H), 1.95 (s, 1H), 1.30, 1.27 (2s, 3H), 0.86–0.80 (m, 6H).

EXAMPLE 3

Z-(2-Me-Ala)-Asp-fmk

The title compound was prepared from Z-DL-2-methylalanine in three-steps as described in Example 1. $^1$H NMR (DMSO-d$_6$): δ 8.00 (br s, 1 H), 7.35 (s, 5 H), 4.99 (s, 2 H), 5.10–4.53 (m, 3 H), 2.88–2.48 (m, 2 H), 1.95 (s, 1 H), 1.30, 1.27 (2s, 3 H), 0.86–0.80 (m, 6H).

EXAMPLE 4

Z-(2-i-Pr-β-Ala)-Asp-fmk

Step A. Ethyl 2-isopropylcyanoacetate. A mixture of ethyl cyanoacetate (2.0 mL, 18.7 mmol), K$_2$CO$_3$ (4.0 g, 28.9 mmol) and 2-iodopropane (3.2 mL, 32.0 mmol) in acetone (30 mL) was refluxed for 48 h. It was diluted with 1:1 hexane/EtOAc (120 mL), washed with water and brine, dried over Na$_2$SO$_4$ and concentrated in vacuo to yield the title compound as a light yellow oil (2.7 g, 17.4 mmol, 93%). $^1$H NMR (CDCl$_3$): δ 4.27 (q, J=7.2, 2H), 3.39 (d, J=5.7, 1H), 2.42 (m, 1H), 1.32 (t, J=7.2, 3H), 1.13 (d, J=7.2, 3H), 1.10 (d, J=6.6, 3H).

Step B. 3-amino-2-isopropylpropionic acid hydrochloride. A mixture of ethyl 2-isopropylcyanoacetate (2.7 g, 17.4 mmol), concentrated HCl (3.0 mL) and PtO$_2$ (107 mg) in ethanol (50 mL) was shaken under hydrogen atmosphere (48.5 psi) for 24 h. The catalyst was filtered out. The filtrate was concentrated in vacuo to about 5 mL and 2N HCl (15 mL) was added. The resulting solution was washed with 1:1 hexane/EtOAc (2×25 mL). The aqueous solution was then refluxed for 24 h, cooled to room temperature, washed with 1:1 hexane/EtOAc (25 mL), concentrated in vacuo to yield the product as a sticky liquid (1.8 g, 10.7 mmol, 61%). $^1$H NMR (DMSO-d$_6$): δ12.74 (s, 1H), 8.03 (s, 2H), 3.01–2.79 (m, 2H), 2.55–2.48 (m, 1H), 2.00 (m, 1H), 0.90–0.87 m, 6H).

The title compound was then prepared in four-steps as described in Example 1 from 3-amino-2-isopropylpropionic acid hydrochloride (2-i-Pr-β-alanine). $^1$H NMR (DMSO-d$_6$): δ 8.33 (br s, 1H), 7.31 (s, 5H), 7.21 (br s, 1H), 4.98 (s, 2H), 5.22–4.97 (m, 1H), 4.64–4.50 (m, 1H), 3.16 (m, 2H), 2.62 (m, 2H), 2.25 (m, 1H), 1.70 (m, 1H), 0.89–0.82 (m, 6H).

EXAMPLE 5

Z-(F$_3$-Val)-Asp-fmk

The title compound was prepared in four-steps as described in Example 1 from 4,4,4-trifluoro-DL-valine (F$_3$-Val). $^1$H NMR (DMSO-d$_6$): δ 12.53 (br s, 1H), 8.74–7.76 (m, 2H), 7.34 (s, 5H), 5.24–4.32 (m, 4H), 5.05 (s, 2H), 2.92–2.58 (m, 3H), 1.24–0.85 (m, 3H).

EXAMPLE 6

Z-(2-Thg)-Asp-fmk

The title compound was prepared in four-steps as described in Example 1 from 2-thienyl-DL-glycine (2-Thg). $^1$H NMR (DMSO-d$_6$): δ 8.80 (m, 1H), 8.08 (br s, 1H), 7.45–6.94 (m, 8H), 5.51 (d, J=7.8, 1H), 5.04 (s, 2H), 5.20–4.80 (m, 2H), 4.55 (m, 1H), 2.62 (m, 2H).

EXAMPLE 7

Z-(2-F-Phg)-Asp-fmk

The title compound was prepared in four-steps as described in Example 1 from 2-fluorophenyl-DL-glycine (2-F-Phg). $^1$H NMR (DMSO-d$_6$): δ12.45 (br s, 1H), 8.73 (s, 1H), 8.10 (s, 1H), 7.33–7.16 (m, 9H), 5.46 (d, J=6.9, 1H), 5.04 (s, 2H), 5.20–4.32 (m, 3H), 2.70–2.40 (m, 2H).

EXAMPLE 8

Z-(L-2-Tha)-Asp-fmk

The title compound was prepared in four-steps as described in Example 1 from 3-(2-thienyl)-L-alanine (2-Tha). $^1$H NMR (DMSO-d$_6$): δ 8.62 (br s, 1H), 7.65 (s, 1H), 7.33–6.90 (m, 7H), 4.99 (s, 2H), 5.20–4.85 (m, 1H), 4.85 (br s, 1H), 4.23 (br s, 1H), 3.19–2.96 (m, 3H), 2.66 (br s, 2H).

EXAMPLE 9

Z-[(R)-Phg]-Asp-fmk

The title compound was prepared in four-steps as described in Example 1 from (R)-phenylglycine ((R)-Phg) as a white solid. $^1$H NMR (DMSO-d$_6$): δ 8.80 (s, 1H), 8.00 (m, 1H), 7.39–7.33 (m, 10H), 5.27 (m, 1 H), 5.03 (s, 2 H), 4.55 (s, 1 H).

EXAMPLE 10

Z-(3-Ph-β-Ala)-Asp-fmk

The title compound was prepared in four-steps as described in Example 1 from (DL)-3-amino-3-phenylpropionic acid (3-ph-β-Ala) as a white solid. $^1$H NMR (DMSO-d$_6$): δ 8.54 (s, 1H), 7.92 (m, 1 H), 7.30 (m, 10 H), 5.04–4.45 (m, 6 H), 2.60–2.58 (m, 2 H).

EXAMPLE 11

Z-(4-Cl-Phg)-Asp-fmk

The title compound was prepared in four-steps as described in Example 1 from (DL)-2-(4-chlorophenyl) glycine (4-Cl-Phg) as a brown solid. $^1$H NMR (DMSO-d$_6$): δ 8.78 (s, 1H), 8.06 (m, 1 H), 7.40–7.33 (m, 9 H), 5.28–5.26 (m, 2 H), 5.03 (s, 2 H), 4.54 (s, 1 H), 2.64 (m, 2 H).

EXAMPLE 12

Z-(4-F-Phg)-Asp-fmk

The title compound was prepared in four-steps as described in Example 1 from (DL)-2-(4-fluorophenyl) glycine (4-F-Phg) as a brown solid (109 mg, 0.25 mmol). $^1$H NMR (DMSO-d$_6$): δ 8.04 (s, 1H), 7.93 (s, 1 H), 7.43–7.33 (m, 9 H), 5.27 (m, 2 H), 5.07 (s, 2 H), 4.54 (s, 1 H), 2.88–2.72 (m, 2 H).

EXAMPLE 13

Z-[(L)-2-Thg]-Asp-fmk

The title compound was prepared in four-steps as described in Example 1 from (L)-(2-thienyl)glycine ((L)-2-Thg) as a brown solid. $^1$H NMR (DMSO-d$_6$): δ 8.80 (s, 1H), 8.10 (s, 1 H), 7.87–7.85 (m, 1 H), 7.34 (m, 5 H), 7.05–6.97 (m, 2 H), 5.51–5.49 (m, 1 H), 5.05 (s, 2 H), 4.74 (s, 2 H), 4.59–4.56 (m, 1 H), 2.78–2.65 (m, 2 H).

EXAMPLE 14

Z-(3-Thg)-Asp-fmk

The title compound was prepared in four-steps as described in Example 1 from (DL)-(3-thienyl)glycine (3-Thg) as a solid. $^1$H NMR (DMSO-d$_6$): δ 8.79 (s, 1H), 8.00 (s, 1 H), 7.34 (m, 5 H), 7.13 (s, 1 H), 5.33 (m, 2 H), 5.04 (s, 2 H), 4.56–4.36 (m, 1 H), 2.70–2.59 (m, 2 H).

EXAMPLE 15

Z-[(L)-3-Thg]-Asp-fmk

The title compound was prepared in four-steps as described in Example 1 from (L)-(3-thienyl)glycine ((L)-3-Thg) as a solid. $^1$H NMR (DMSO-d$_6$): δ 8.77 (s, 1 H), 7.99 (s, 1 H), 7.34 (m, 5 H), 7.14 (s, 1 H), 5.33 (m, 1 H), 5.04 (s, 2 H),4.56(m, 1 H).

EXAMPLE 16

Z-[(L)-3-CN-Ala]-Asp-fmk

The title compound was prepared in four-steps as described in Example 1 from (L)-3-cyano-alanine ((L)-3-CN-Ala) as a brown solid. $^1$H NMR (DMSO-d$_6$): δ 8.59 (s, 1H), 7.97–7.82 (m, 1 H), 7.34 (m, 5 H), 5.06 (s, 2 H), 4.54 (s, 1 H), 4.38 (s, 1 H), 2.93–2.81 (m, 2 H), 2.61 (m, 2 H).

EXAMPLE 17

Z-[(L)-1-Nal]-Asp-fmk

The title compound was prepared in four-steps as described in Example 1 from (L)-3-(1-naphthyl)-alanine as a brown solid. $^1$H NMR (DMSO-d$_6$): δ 8.19–8.17 (m, 1H), 7.93–7.29 (m, 14 H), 4.92 (s, 2 H), 4.61–4.36 (s, 3 H), 3.45 (m, 2 H), 2.72 (m, 2 H).

EXAMPLE 18

Z-[(L)-Cha]-Asp-fmk

The title compound was prepared in four-steps as described in Example 1 from (L)-3-cyclohexylalanine as a brown solid. $^1$H NMR (DMSO-d$_6$): δ 7.33 (m,5H),5.02(s, 2H),4.02(s, 1 H),2.73 (m,2H), 1.61–1.12(m, 13 H).

EXAMPLE 19

Z-[(L)-3-Cl-Ala]-Asp-fmk

The title compound was prepared in four-steps as described in Example 1 from (L)-3-chloroalanine as a brown solid. $^1$H NMR (DMSO-d$_6$): δ 7.92 (s, 1 H), 7.63 (s, 1H), 7.34 (m, 5 H), 5.04 (s, 2 H), 2.72 (m, 2 H).

EXAMPLE 20

Z-(3-F-Ala)-Asp-fmk

The title compound was prepared in four-steps as described in Example 1 from (DL)-3-fluoroalanine as a brown solid. $^1$H NMR (DMSO-d$_6$): δ 7.95–7.66 (m, 1H), 7.35 (m, 5 H), 5.05 (s, 2 H), 4.63–4.47 (m, 1 H).

EXAMPLE 21

Z-(3-CF$_3$-Ala)-Asp-fmk

The title compound was prepared in four-steps as described in Example 1 from 2-amino-4,4,4-trifluorobutyric acid (3-CF$_3$-Ala) as a brown solid. $^1$H NMR (DMSO-d$_6$): δ 7.86–7.84 (d, 1 H), 7.62–7.59 (d, 1 H), 7.34 (m, 5 H), 5.05 (s, 2 H), 4.57 (s, 1 H), 2.72–2.65 (m, 2 H).

EXAMPLE 22

Z-(4-CF$_3$-Phg)-Asp-fmk

The title compound was prepared in four-steps as described in Example 1 from 4-trifluoromethylphenylglycine (4-CF$_3$-Phg) as a solid. $^1$H NMR (DMSO-d$_6$): δ 8.86 (s, 1 H), 8.18 (s, 1 H), 7.70–7.64 (m, 4 H), 7.34 (m, 5 H), 5.42 (s, 1 H), 5.04 (s, 2 H), 4.55 (s, 1 H).

EXAMPLE 23

Z-(3-Me$_2$N-Ala)-Asp-fmk

The title compound was prepared in four-steps as described in Example 1 from (DL)-dimethylamino-alanine (3-Me$_2$N-Ala) as a solid. $^1$H NMR (DMSO-d$_6$): δ 7.40–7.34 (m, 5 H), 5.06–4.99 (m, 3 H), 4.57–4.37 (m, 1 H), 2.60 (s, 10 H).

EXAMPLE 24

Z-[3-F-3-Me-Ala]-Asp-fmk

The title compound was prepared in four-steps as described in Example 1 from 2-amino-3-fluorobutyric acid (3-F-3-Me-Ala) as a solid. $^1$H NMR (DMSO-d$_6$): δ 8.54 (s, 1 H), 7.74–7.68 (m, 1 H), 7.34 (m, 5 H), 5.03 (s, 2 H), 4.54 (s, 1 H), 2.55 (m, 2 H), 1.39–1.22 (m, 3 H).

EXAMPLE 25

Z-[(L)-Chg]-Asp-fmk

The title compound was prepared in four-steps as described in Example 1 from (L)-cyclohexylglycine ((L)-Chg) as a yellow solid. $^1$H NMR (DMSO-d$_6$): δ 8.38 (s, 1 H), 7.33 (m, 5 H), 5.00 (s, 2 H), 4.56–4.44 (m, 1 H), 3.86–3.80 (m, 1 H), 2.67 (m, 2 H), 1.62–1.56 (m, 11 H).

EXAMPLE 26

Z-(2-Fug)-Asp-fmk

The title compound was prepared in four-steps as described in Example 1 from 2-furyl-Gly. $^1$H NMR (DMSO-d$_6$): δ 8.59 (br s, 1 H), 8.09–7.47 (m, 3 H), 7.32–7.26 (m, 5 H), 6.94 (m, 1 H), 6.41–6.33 (m, 2 H), 5.36 (m, 1 H), 5.20–4.95 (m, 2 H), 5.04 (s, 2 H), 5.46 (m, 1 H), 2.56–2.40 (m, 2H).

EXAMPLE 27

Z-(3-F-Val)-Asp-fmk

The title compound was prepared in four-steps as described in Example 1 from 3-fluoro-Val. $^1$H NMR (DMSO-d$_6$): δ 8.57 (br s, 1 H), 7.85–7.57 (m, 1 H), 7.39 (s, 5 H), 7.08 (s, 2 H), 4.59 (m, 1 H), 4.33 (m, 1 H), 2.65 (m, 2 H), 1.35 (d, J=21.9, 6H).

EXAMPLE 28

Z-(2-Abu)-Asp-fmk

The title compound was prepared in four-steps as described in Example 1 from 2-aminobutyric acid (Abu) as a white solid. $^1$H NMR (DMSO-d$_6$), δ 0.831 (t, 3H, J=7), 1.60 (m, 2H), 2.90 (m, 1H), 4.47 (m, 1H), 5.01 (m, 2H), 5.20 (m, 1H), 7.34 (s, 5H), 7.48 (m, 1H), 8.23 (m, 1H).

EXAMPLE 29

Z-Tle-Asp-fmk

The title compound was prepared in four-steps as described in Example 1 from tert-Leucine (Tle). $^1$H NMR (DMSO-d$_6$): δ 8.51 (br s, 1H), 7.36 (br s, 5H), 5.04 (br s, 2H), 5.30–4.95 (m, 2H), 4.63 (br s, 1H), 3.89 (s, 1H), 2.80–2.50 (m, 2H), 0.91 (s, 9H).

EXAMPLE 30

Z-Cpg-Asp-fmk

The title compound was prepared in four-steps as described in Example 1 from cyclopentylglycine (Cpg). $^1$H NMR (DMSO-d$_6$): δ 7.37–7.28 (m, 5H), 6.85 (d, J=7.5, 1H), 5.12–5.03 (m, 2H), 5.09 (s, 2H), 4.84 (br s, 1H), 4.07 (m, 1H), 2.90–2.75 (m, 2H), 2.28 (m, 1H), 1.80–1.30 (m, 8H).

EXAMPLE 31

Enzyme Activity

The activity of Cbz-Phg-Asp-fmk as an inhibitor of caspase-3 (CPP32) was measured in a fluorometric enzyme assay. Recombinant caspase-3 protein was prepared by expressing DNA clones encoding these enzymes in an insect host cell (sf9 cells) using baculovirus as the vector. See, Webb, N.R. et al., "Expression of proteins using recombinant Baculovirus," *Techniques* 2:173–188 (1990). Enzyme activity was measured using synthetic peptide substrates attached to a fluorogenic leaving group. Cleavage of the synthetic substrate by the enzyme results in a fluorescent signal which is read in a spectrofluorometer or in a fluorometric microtiter plate reader.

Caspase-3 activity was measured using the following buffer conditions: 100 mM HEPES pH 7.5, with 10% sucrose, 1% CHAPS. The peptide substrate for caspase-3 is Asp-Glu-Val-Asp-AMC (SEQ ID NO:2). Substrate was used at the $K_m$ concentrations of 5 μM. The assay for enzyme activity was typically carried out at 30° C. for 30 minutes.

Table II lists the IC$_{50}$ of Cbz-Phg-Asp-fmk and other dipeptide as inhibitor of caspase-3.

TABLE II

Activity of Dipeptide as Inhibitor of Caspase-3

| Name | Caspase-3 IC$_{50}$ ($\mu$M) |
|---|---|
| Z—[(S)—Phg]—Asp—fmk | 0.10 |
| Z-(2-Me—Val)—Asp—fmk | 2.3 |
| Z-(2-Me—Ala)—Asp—fmk | 1.4 |
| Z-(2-i-Pr— —Ala)—Asp—fmk | 1.4 |
| Z—(F$_3$—Val)—Asp—fmk | 0.60 |
| Z-(2-Thg)—Asp—fmk | 0.28 |
| Z-(2-F—Phg)—Asp—fmk | 0.36 |
| Z-(L-Tha)—Asp—fmk | 0.15 |
| Z-[(R)-Phg]—Asp—fmk | 0.39 |
| Z-(2-Fug)—Asp—fmk | 0.44 |
| Z-(3-Ph— —Ala)—Asp—fmk | 4.7 |
| Z-(4-Cl—Phg)—Asp—fmk | 0.27 |
| Z-(4-F-Phg)—Asp—fmk | 1.2 |
| Z-[(L)-Chg]—Asp—fmk | 0.10 |
| Z-(3-F-Val)—Asp—fmk | 0.44 |
| Z-[(L)-2-Thg]—Asp—fmk | 0.51 |
| Z-(3-Thg)—Asp—fmk | 0.34 |
| Z-[(L)-3-Thg]—Asp—fmk | 0.26 |
| Z-[(L)-3-CN—Ala]—Asp—fmk | 0.53 |
| Z-[(L)-1-Nal]—Asp—fmk | 1.0 |
| Z-[(L)-3-Cl—Ala]—Asp—fmk | 1.0 |
| Z-[(L)-Chg]—Asp—fmk | 0.90 |
| Z-(3-F-Ala)—Asp—fmk | 0.9 |
| Z-(3-CF$_3$—Ala)—Asp—fmk | 2.6 |
| Z-(4-CF$_3$—Phg)—Asp—fmk | 1.2 |
| Z-(3-Me$_2$N—Ala]—Asp—fmk | 9.6 |
| Z-(3-F-3-Me—Ala)—Asp—fmk | 0.48 |
| Z-2-Abu—Asp—fmk | 0.10 |

EXAMPLE 32

In Vivo Activity

Cbz-Phg-Asp-fmk was examined as a protectant against lethality in mice caused by an anti-Fas antibody (clone Jo2) (Rodriguez, I. et al *J. Exp. Med* 184:2067–2072 (1996). Swiss Webster female mice weighing between 16–20 g were used. Food and water were given ad libium. Purified hamster anti-mouse Fas monoclonal antibody (clone Jo2, commercially available) 1 mg/ml in phosphate buffered saline was dosed i.v. at 6 $\mu$g/mouse (80 $\mu$l).

Cbz-Phg-Asp-fmk was dissolved in 0.05M Tris base adjusted to pH 8.5 with HCl. The concentration of Cbz-Phg-Asp-fmk was 1–10 mg/ml dosed as a single bolus i.v. in a volume of 1–5 $\mu$l/g body weight. Five groups of mice were injected with 6 $\mu$g of Fas antibody per mouse. 5 minutes following the antibody injection the mice received either Tris vehicle control or 1, 2.5, 10 or 50 mg/kg of Cbz-Phg-Asp-fmk. The survival of the mice was followed throughout 24 hours.

Table III lists the percent survival of mice treated with Cbz-Phg-Asp-Fmk.

TABLE III

Percent survival over time due to administration of Cbz-Phg-Asp-fmk

| | Vehicle control | 1 mg/kg/i.v. | 2.5 mg/kg/i.v. | 10 mg/kg/i.v. | 50 mg/kg/i.v. |
|---|---|---|---|---|---|
| 1 h | 0% | 100% | 100% | 100% | 100% |
| 3 h | — | 14.3% | 28.6% | 42.9% | 100% |
| 24 h | — | 0% | 0% | 14.3% | 42.9% |

The results in Table III show that a compound of the present invention is a potent inhibitor of antiFas induced lethality in mice.

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound of Formula II:

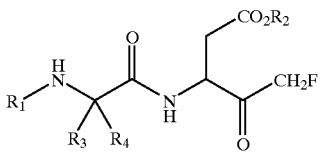

II or a pharmaceutically acceptable salt or prodrug thereof, wherein $R_1$ is an N-terminal protecting group; $R_2$ is an optionally substituted alkyl or H; and $R_3$ and $R_4$ independently are haloalkyl, aryl, heteroaryl, $C_{1-10}$alkyl, alkenyl, alkynyl, aralkyl, aralkenyl, aralkynyl or hydroxyalkyl.

2. The compound of claim 1, selected from the group consisting of:
Z-(2-Me-Val)-Asp-fmk and
Z-(2-Me-Ala)-Asp-fmk.

3. A compound of Formula III:

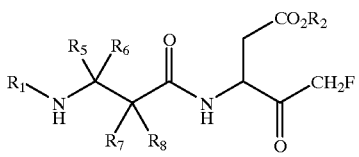

III or a pharmaceutically acceptable salt or prodrug thereof, wherein $R^1$ is an N-terminal protecting group; $R_2$ is an optionally substituted alkyl or H; $R_5$, $R_6$, $R_7$ and $R_8$ independently are hydrogen, haloalkyl, aryl, heterocyclic, heteroaryl, $C_{1-10}$alkyl, alkenyl, alkynyl, aralkyl, aralkenyl, aralkynyl or hydroxyalkyl;
provided that at least one of the $R_5$–$R_8$ is other than hydrogen.

4. The compound of claim 3, selected from the group consisting of:
Z-(2-i-Pr-β-Ala)-Asp-fmk and
Z-(3-Ph-β-Ala)-Asp-fmk.

5. A compound of Formula IV:

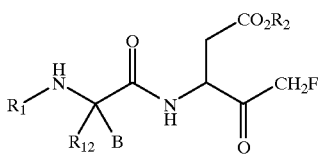

IV or a pharmaceutically acceptable salt or prodrug thereof, wherein $R_1$ is an N-terminal protecting group; $R_2$ is an optionally substituted alkyl or H; $R_{12}$ is hydrogen or $C_{1-10}$ alkyl; B is aryl, heteroaryl, saturated or partially unsaturated carbocycle or saturated or partially unsaturated heterocycle which is optionally substituted by hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, cyano, $C_1$–$C_6$ acylamino, hydroxy, $C_1$–$C_6$ acyloxy, $C_1$–$C_6$ alkoxy, alkylthio, or carboxy.

6. The compound of claim 5, wherein $R_1$ is t-butyloxycarbonyl, acetyl or benzyloxycarbonyl.

7. The compound of claim 5, wherein $R_2$ is H, Me or acetoxymethyl.

8. The compound of claim 5, wherein B is an optionally substituted phenyl or cyclohexyl.

9. The compound of claim 5, wherein $R_{12}$ is H.

10. The compound of claim 5, selected from the group consisting of:
Boc-Phg-Asp-fmk,
Boc-(2-F-Phg)-Asp-fmk,
Ac-Phg-Asp-fmk,
Ac-(2-F-Phg)-Asp-fmk,
Z-Phg-Asp-fmk,
Z-(2-F-Phg)-Asp-fmk,
Z-Chg-Asp-fmk,
Z-(2-Fug)-Asp-fmk,
Z-(4-F-Phg)-Asp-fmk,
Z-(4-Cl-Phg)-Asp-fmk,
Z-(3-Thg)-Asp-fmk,
Z-(4-CF$_3$-Phg)-Asp-fmk,
Z-Cpg-Asp-fmk,
Z-Cbg-Asp-fmk and
Z-(2-Thg)-Asp-fmk.

11. A compound of Formula V:

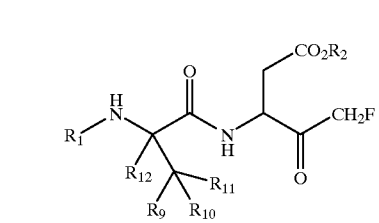

V or a pharmaceutically acceptable salt or prodrug thereof, wherein $R_1$ is an N-terminal protecting group; $R_2$ is an optionally substituted alkyl or H; $R_{12}$ is hydrogen or $C_{1-10}$ alkyl; $R_9$, $R_{10}$ and $R_{11}$ are independently hydrogen, $C_{1-10}$alkyl, halogen, haloalkyl, aryl, heteroaryl, saturated or partially unsaturated carbocycle or saturated or partially unsaturated heterocycle; provided that at least one of $R_9$–$R_{11}$ is halogen, haloalkyl, heteroaryl, saturated or partially unsaturated carbocycle or saturated or partially unsaturated heterocycle.

12. The compound of claim 11, wherein $R_1$ is t-butyloxycarbonyl, acetyl or benzyloxycarbonyl.

13. The compound of claim 11, wherein $R_2$ is H, Me or acetoxymethyl.

14. The compound of claim 11, wherein $R_2$ is H.

15. The compound of claim 11, wherein $R_{12}$ and $R_9$ are H, $R_{10}$ is alkyl or haloalkyl, and $R_{11}$ is $CF_3$.

16. The compound of claim 11, wherein $R_{12}$ is H, $R_9$ and $R_{10}$ independently are hydrogen, alkyl or haloalkyl, and $R_{11}$ is F or heteroaryl.

17. The compound of claim 11, selected from the group consisting of:
Boc-(F$_3$-Val)-Asp-fmk,
Boc-(3-F-Val)-Asp-fmk,
Ac-(F$_3$-Val)-Asp-fmk,
Ac-(3-F-Val)-Asp-fmk,
Z-(3-F-Val)-Asp-fmk,
Z-(3-Cl-Ala)-Asp-fmk,
Z-(3-F-Ala)-Asp-fmk,
Z-(F$_3$-Ala)-Asp-fmk,
Z-(3-F-3-Me-Ala)-Asp-fmk,
Z-(3-Cl-3-F-Ala)-Asp-fmk,
Z-(3-CF$_3$-Ala)-Asp-fmk,
Z-Tle-Asp-fmk, Z-($F_3$-Val)-Asp-fmk;
Z-(2-Fua)-Asp-fmk,
Z-(2-Tha)-Asp-fmk,
Z-(3-Fua)-Asp-fmk,
Z-(3-Tha)-Asp-fmk and
Z-Cha-Asp-fmk.

18. A compound selected from the group consisting of:
Z-(3-CN-Ala)-Asp-fmk,
Z-(1-Nal)-Asp-fmk,
Z-(3-$Me_2$N-Ala)-Asp-fmk,
Z-(2-Abu)-Asp-fmk and
Z-Thz-Asp-fmk.

19. A pharmaceutical composition, comprising a compound of claim 1, 3, 5, 11 or 18 and a pharmaceutically acceptable carrier.

20. A method of inhibiting cell death of a cell or tissue, comprising contacting said cell or tissue with an effective amount of a compound of claim 1, 3, 5, 11 or 18.

21. A method of treating or ameliorating cell death in the central or peripheral nervous system, retinal neurons, cardiac muscle or immune system cells of an animal, comprising administering to the animal in need of such treatment or ameliorating an effective amount of a compound of claim 1, 3, 5, 11 or 18.

22. The method of claim 21, where in said cell death is in the central or peripheral nervous system, and is due to one of:
(a) a condition of ischemia and excitotoxicity selected from the group consisting of focal ischemia due to stroke and global ischemia due to cardiac arrest;
(b) traumatic injury;
(c) viral infection;
(d) radiation-induced nerve cell death;
(e) a neurodegenerative disorder selected from the group consisting of Alzheimer's disease, Parkinson's Disease, a prion disease, multiple sclerosis, amyotrophic lateral sclerosis, and spinobulbar atrophy; or
(f) spinal cord injury.

23. The method of claim 21, wherein said cell death is in the central or peripheral nervous system, and is due to expansion of trinucleotide repeats of a gene.

24. The method of claim 21, wherein said cell death is due to Huntington's Disease.

25. The method of claim 21, wherein said cell death is in cardiac muscle tissue, and is due to myocardial infarction, congestive heart failure, cardiomyopathy or viral infection of the heart.

26. The method of claim 21, wherein said cell death is in retinal neurons and is due to increased intraocular pressure, age-related macular degeneration or retinitis pigmentosa.

27. The method of claim 21, wherein said cell death is in the immune system, and is due to an immune deficiency disorder selected from the group consisting of acquired immune deficiency syndrome, severe combined immune deficiency syndrome and radiation-induced immune suppression.

28. The method of claim 21, wherein said cell death is due to an autoimmune disorder selected from the group consisting of lupus erythematosus, rheumatoid arthritis and type I diabetes.

29. The method of claim 21, wherein said cell death is due to type I diabetes.

30. A method of treating or preventing polycystic kidney disease, renal amyloidosis, acute renal failure, cyclosporine A induced tubular epithelial cell death, HIV-induced nephropathy or anemia/erythropoiesis in an animal, comprising administering to the animal in need of such treatment or preventing an effective amount of a compound of claim 1, 3, 5, 11 or 18.

31. A method of protecting a mammalian organ or tissue from cell death due to deprivation of normal blood supply, comprising contacting said organ or tissue with an effective amount of a compound of claim 1, 3, 5, 11 or 18.

32. The method of claim 31, wherein said organ or tissue is present in a storage medium prior to transplant into a mammal.

33. The method of claim 31, wherein said contacting comprises infusion of said compound into the organ or tissue, or bathing of said organ or tissue in a storage medium which comprises said compound.

34. A method of reducing or preventing cell death in a donor organ or tissue after it has been transplanted into a host due to the effects of host immune cells, comprising administering to said host in need thereof an effective amount of a compound of claim 1, 3, 5, 11 or 18.

35. A method of reducing or preventing the death of mammalian sperm or eggs used in in vitro fertilization procedures, comprising contacting said sperm or egg with an effective amount of a compound of claim 1, 3, 5, 11 or 18.

36. A method of extending the lifespan of a mammalian or yeast cell line, comprising contacting said cell line with a compound of claim 1, 3, 5, 11 or 18.

37. The method of claim 36, wherein said contacting comprises including said compound in a cell growth medium.

38. A method of treating or ameliorating hair loss or premature graying of the hair in a mammal, comprising contacting the hair or hair follicles of the mammal in need thereof with a compound of claim 1, 3, 5, 11 or 18.

39. The method of claim 38, wherein hair loss is treated, and said hair loss is due to male-pattern baldness, radiation, chemotherapy or emotional stress.

40. A method of treating or ameliorating skin damage of a mammal due to exposure to high levels of radiation, heat or chemicals, comprising applying to the skin of the mammal in need thereof a compound of claim 1, 3, 5, 11 or 18.

41. The method of claim 40, wherein said compound is applied as part of an ointment.

42. The method of claim 40, wherein said skin damage is due to acute over-exposure to the sun, and wherein said treating reduces blistering and peeling of the skin.

43. A method of treating or ameliorating sepsis in an animal, comprising administering to the animal in need thereof an effective amount of a compound of claim 1, 3, 5, 11 or 18.

44. A method of treating or ameliorating hepatitis in an animal, comprising administering to the animal in need thereof an effective amount of a compound of claim 1, 3, 5, 11 or 18.

45. A method of treating or ameliorating hereditary tyrosinemia type 1 in an animal, comprising administering to the animal in need thereof an effective amount of a compound of claim 1, 3, 5, 11 or 18.

46. A method of treating or ameliorating chronic alcohol ingestion induced buccal mucosa cell death in an animal, comprising administering to the animal in need thereof an effective amount of a compound of claim 1, 3, 5, 11 or 18.

47. A method of treating or ameliorating cell death in plants or flowers, comprising administering to the plants or flowers in need thereof an effective amount of a compound of claim 1, 3, 5, 11 or 18.

48. A method of treating or ameliorating radiation or ultraviolet-irradiation induced cell death in an animal, comprising administering to the animal in need thereof an effective amount of a compound of claim 1, 3, 5, 11 or 18.

49. A method of treating or ameliorating apoptotic death of bone marrow cells in myelodysplastic syndromes (MDS), comprising administering to the animal in need thereof an effective amount of a compound of claim 1, 3, 5, 11 or 18.

* * * * *